US009957350B2

(12) United States Patent
Gobius Du Sart et al.

(10) Patent No.: US 9,957,350 B2
(45) Date of Patent: May 1, 2018

(54) METHOD TO MANUFACTURE PLA USING A NEW POLYMERIZATION CATALYST

(71) Applicant: PURAC Biochem BV, Gorinchem (NL)

(72) Inventors: Gerrit Gobius Du Sart, Gorinchem (NL); Matthew Gwilym Davidson, Bath (GB); Christopher James Chuck, Bristol (GB)

(73) Assignee: PURAC BIOCHEM BV, Gorinchem (NL)

( * ) Notice: Subject to any disclaimer, the term of this patent is extended or adjusted under 35 U.S.C. 154(b) by 0 days. days.

(21) Appl. No.: 14/888,460

(22) PCT Filed: Apr. 29, 2014

(86) PCT No.: PCT/EP2014/058688
§ 371 (c)(1),
(2) Date: Nov. 2, 2015

(87) PCT Pub. No.: WO2014/177543
PCT Pub. Date: Nov. 6, 2014

(65) Prior Publication Data
US 2016/0075821 A1  Mar. 17, 2016

(30) Foreign Application Priority Data
May 2, 2013  (EP) .................................. 13166273

(51) Int. Cl.
| C08G 63/08 | (2006.01) |
| C08G 63/85 | (2006.01) |
| C08G 18/42 | (2006.01) |
| C08G 63/82 | (2006.01) |
| C08F 4/76 | (2006.01) |
| C07F 7/00 | (2006.01) |

(52) U.S. Cl.
CPC .......... *C08G 63/85* (2013.01); *C08G 18/428* (2013.01); *C08G 63/08* (2013.01); *C08G 63/823* (2013.01); *C07F 7/006* (2013.01); *C08F 4/76* (2013.01); *C08F 2410/03* (2013.01)

(58) Field of Classification Search
CPC .......... C08F 4/76; C08F 2410/03; C07F 7/00; C07F 7/006; C08G 18/428; C08G 63/08
See application file for complete search history.

(56) References Cited

U.S. PATENT DOCUMENTS

| 2005/0009687 A1 | 1/2005 | Verkade et al. |
| 2007/0021585 A1 | 1/2007 | Chen |
| 2009/0247710 A1* | 10/2009 | De Vos ................ C08G 63/912 525/450 |

| 2010/0331512 A1 | 12/2010 | Rafler et al. |
| 2012/0270048 A1 | 10/2012 | Saigusa et al. |
| 2012/0309929 A1 | 12/2012 | Hayashi et al. |

FOREIGN PATENT DOCUMENTS

| WO | WO2009121830 A1 | 10/2009 |
| WO | WO2012076140 A1 | 6/2012 |

OTHER PUBLICATIONS

Gendler et al (Titanium and Zirconium Complexes of Dianionic and Trianionic Amine-Phenolate-Type Ligands in Catalysis of Lactide Polymerization, Inorganic Chemistry, vol. 45, No. 12, 2006, pp. 4783-4790), Dec. 2006.*
Chmura et al (Highly active and stereoselective zirconium and hafnium alkoxide initiators for solvent-free ring-opening polymerization of rac-lactide, Chem. Commun., 2008, 1293-1295 | 1293), Jun. 2008.*
International Search Report and Written Opinion; dated Jul. 3, 2014 for PCT Application No. PCT/EP2014/058688.
Davidson, Matthew G., et al. "Isolation and characterisation of transition and main group metal complexes supported by hydrogen-bonded zwitterionic polyphenolic ligands." Chemical Communications 15 (2003): 1832-1833.
Canadian Office Action; dated Mar. 6, 2017 for CA Application No. CA 2,910,710.

(Continued)

*Primary Examiner* — Gregory Listvoyb
(74) *Attorney, Agent, or Firm* — Mendelsohn Dunleavy, P.C.

(57) ABSTRACT

The invention relates to a method for manufacturing polylactide, comprising the steps of mixing lactide and a metal-coordination compound as polymerization catalyst to obtain a reaction mixture, polymerizing the lactide in liquid phase at a temperature of at least 150° C. to form polylactide in liquid phase and allowing the polylactide to solidify, characterized in that the polymerization catalyst comprises a metal-ligand coordination compound whereby the parent ligand answers the formula (I), whereby R represents an H atom, an aliphatic group, a halide atom or a nitro group and the metal is at least one of Zr and Hf. The invented catalysts show kinetics which is comparable to the kinetics of the known Sn-octoate catalyst.

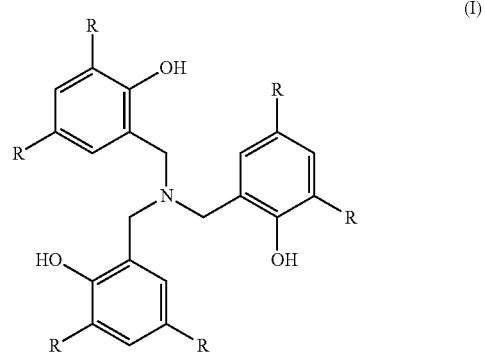

(I)

19 Claims, 2 Drawing Sheets

(56) References Cited

OTHER PUBLICATIONS

Figure 1:
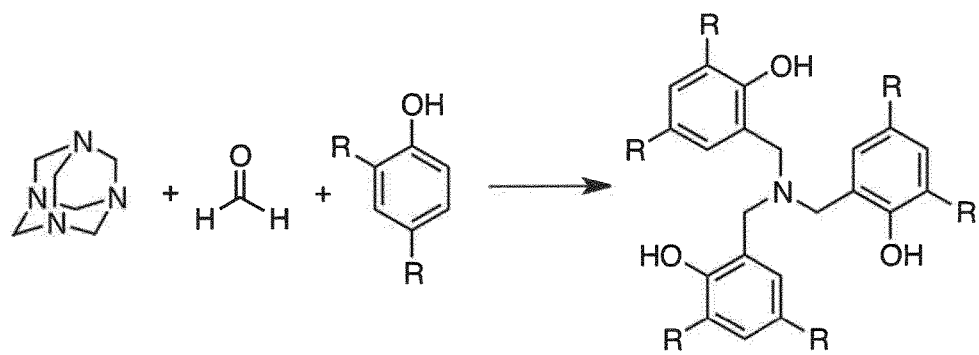

Singapore Written Opinion; dated Sep. 16, 2016 for SG Application No. SG 11201508918V.
Chinese Office Action; dated Sep. 9, 2016 for CN Application No. CN 201480031589.
New Zealand Examination Report; dated May 11, 2016 for NZ Application No. NZ 713759.
Korean Office Action; dated Aug. 8, 2016 for KR Application No. 10-2015-7033902.

* cited by examiner

METHOD TO MANUFACTURE PLA USING A NEW POLYMERIZATION CATALYST

FIELD OF THE INVENTION

The invention relates to a method for manufacturing polylactide, comprising the steps of mixing lactide and a metal-coordination compound as polymerization catalyst to obtain a reaction mixture, polymerizing the lactide in liquid phase at a temperature of at least 150° C. to form polylactide in liquid phase and allowing the polylactide to solidify. The invention also relates to the use of such metal-coordination compound as a polymerization catalyst in the production of polylactide. The invention further relates to polylactide having a high thermal stability and low racemization rate.

BACKGROUND OF THE INVENTION

Currently much attention is devoted to polylactide (also referred to as polylactic acid and abbreviated as PLA). PLA is an aliphatic polyester, which in essence can be manufactured from renewable resources. Such manufacture may involve the fermentation of starch, sugar or other renewable organic substrates into lactic acid. PLA can in principle be synthesized by direct polycondensation of lactic acid (lactate monomers), which has the drawback that a high molecular weight is not easily reached. Therefore, PLA is usually prepared by ring-opening polymerization of lactide, the cyclic dimer of lactic acid. Lactide is usually manufactured by polycondensation of lactic acid into PLA oligomers, followed by de-polymerization of these oligomers by a so-called 'backbiting' mechanism in the presence of a suitable catalyst. After purification, the produced lactide can be converted into PLA of controlled molecular weight by means of a ring-opening polymerization reaction (ROP) in the presence of a polymerization catalyst. The latter method can be used to manufacture PLA of high molecular weight. Especially the compound stannous octoate or tin-octoate $(Sn(Oct)_2$ or stannous bis(2-ethyl-hexoate) is well-known as a polymerization catalyst in the manufacture of PLA under industrial large volume conditions.

A method as described in the opening paragraph is known as such, by example form the European patent publication WO2009/121830-A1 in the name of the current applicant, in which the well-known $SnOct_2$ is used as polymerization catalyst. When the polymerization conditions are properly chosen, high quality PLA can be obtained by means of the known method. Under such conditions, the use of Sn-octoate as catalyst in a lactide-to-PLA process results in a desired fast polymerization rate resulting in a polymer resin having a relatively high melt stability and low racemization rate.

Although the mentioned Sn-octoate catalyst may function well under optimized polymerization conditions, there appears to be much interest in alternative catalyst systems in order to broaden the possibilities in the manufacture of PLA grades having different or improved properties or characteristics. More specifically, there is a clear interest in Sn-free catalyst systems for polymerization of lactide into PLA. Such alternative catalysts should however be able to provide reaction kinetics comparable with the reaction rates achieved with the known tin-octoate. Additionally, the thermal stability of the PLA manufactured with such alternative catalyst systems should also be high, and preferably higher than reached with PLA produced with tin-octoate. Further, the alternative catalyst systems should not or hardly induce racemization of the lactoyl moieties in the polylactide.

SUMMARY OF THE INVENTION

It is an object of the present invention to provide a new catalyst system which can suitably be used in the polymerization of lactide to PLA in the liquid phase. Said new catalyst system should preferably show good or even improved polymerizing properties as compared with the process in which the well-known Sn-octoate compound is used as catalyst while performing the polymerization in the liquid phase. PLA produced with help of the new catalyst should preferably have a high thermal stability and a low racemization rate.

These and possible other objects of the present invention are achieved by means of a method for manufacturing polylactide, comprising the steps of mixing lactide and a metal-coordination compound as polymerization catalyst to obtain a reaction mixture, polymerizing the lactide in liquid phase at a temperature of at least 150° C. to form polylactide in liquid phase and allowing the polylactide to solidify, characterized in that the polymerization catalyst comprises a metal-ligand coordination compound whereby the parent ligand answers the formula I,

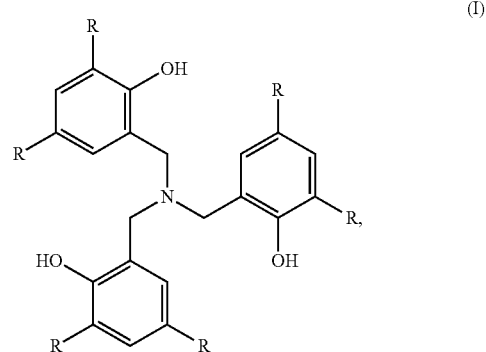

whereby the metal is at least one of Zr and Hf and whereby R represents an H atom, an aliphatic group, a halide atom or a nitro group. Both Zr and Hf are bonded in the metal coordination compounds as metal ions. It is noted that in the metal-ligand coordination compound, the ligand is anionic (i.e. negatively charged and lacking the protons on the hydroxyl groups). For that reason, the ligand in the formula is indicated as being the parent ligand.

The invention is based on the surprising finding that the presently claimed class of compounds can suitably be used as catalysts in the polymerization of lactide to PLA in the liquid phase. The thermal stability of the PLA manufactured with the help of said new polymerization catalyst moreover appears to be at least comparable with the thermal stability obtained with PLA produced by means of the known Sn-octoate compound. The polymerization kinetics of the new catalyst system match the kinetics observed in the manufacture of PLA with the known production process, provided that the proper polymerization conditions are chosen. The amount of racemization performed during the polymerization process is negligible and at least of the same low magnitude as reached with the known process.

It is noted that the R groups of the aryl moieties in the ligand preferably consist of an H atom, or a short alkyl group. In latter situation, ethyl-, n-propyl-, iso-propyl-, or tert-butyl groups are suitable candidates. The various R-groups of the same or of the different benzyl-group may be identical or different. The mentioned short alkyl group may contain substituents, like halogen atoms, etc. An interesting ligand in this respect is tris(-3,5-di-tert-butyl-2-hydroxybenzyl)amine.

It is noted that the patent publication US2005/0009687-A1 describes a series of $Ti^{4+}$ coordination compounds having similar ligands which are used as a polymerization catalyst in the manufacture of PLA from lactide, both in bulk polymerization and solution polymerization. The yield of the bulk polymerization reaction is however quite low in comparison with the presently invented method. Moreover, high amounts of Ti-catalyst are needed for obtaining acceptable polymerization kinetics. In the presently invented process, catalyst loading are typically 100 times lower than the catalyst loadings disclosed in the prior art publication.

An interesting embodiment of the method according to the present invention is characterized in that the aliphatic group is a methyl group. Catalysts with optimal polymerization features may be obtained in case that all R groups in the ligand of the metal-ligand coordination compound are methyl groups. In such situation, one metal center is coordinated with two ligands. This results in the formation of so-called zwitterionic structures. The ligand used for this embodiment of the invented method can also be described as tris(-3,5-dimethyl-2-hydroxybenzyl)amine.

Without being bound to theory, the inventors believe that the specific metal zwitterion structure may contribute to the interesting properties of the new polymerization catalyst. More specifically, the zwitterionic structures, in which one metal center is complexed with two ligands, contain no polymerization-initiating groups by itself. Rather, the complex is expected to form a more active species at higher temperatures, which forms the actual catalytic center. The described class of metal-ligand coordination compounds having this type of ligands is especially interesting in view of their simple, straightforward production and compound stability under storage conditions.

Another interesting embodiment of the presently invented method is characterized in that the metal ion is Zr. According to experimental data, the reaction kinetics is optimal under the claimed conditions. Thus rather short reaction times are needed during the polymerization of lactide in liquid phase to PLA. The use of the Zr coordination compounds with these ligands in the lactide-to-PLA process of the present invention appears to result in almost exclusively isotactic PLA, i.e., the homopolymer of the used lactide diastereomer. It is noted that the composition and structure of one of the mentioned Zr coordination compound is described in "Isolation and characterisation of transition and main group metal complexes supported by hydrogen-bonded zwitterionic polyphenolic ligands" in Chem. Commun., 2003, 1832-1833.

It is noted that lactide can exist in three different geometric structures, which have a diastereomeric relationship. These different structures can be distinguished as R,R-lactide (or D-lactide), S,S-lactide (or L-lactide) and R,S-lactide (or meso-lactide). Within the scope of the present invention, both the pure lactides (being composed of only one diastereomer) can be used in the manufacturing method as well as mixtures of two or of all pure lactides.

It is stressed that the mixture may also contain other reactants than lactide. Interesting polymers can be made in case that the mixture also contains related cyclic esters like glycolide. Another useful reactive monomer may be caprolactone. Valuable co-polymers for the application in the medical area can be manufactured when using these or related reactants together with lactide. It is however preferred that the major part of the monomers consists of lactide, and most preferred lactide amounts for more than 90% of the monomers.

Also interesting is the embodiment of the presently invented method, which is characterized in that a co-initiator is added to the mixture. Suitable co-initiators are alcohols, especially primary alcohols like benzyl alcohol, 1-hexanol, 2-ethylhexanol and dodecanol and/or amines, especially primary amines like hexyl amine and dodecylamine. The co-initiator causes a further increase in the reaction rate and can be used in controlling the intended molecular weight of the PLA to be manufactured. The person skilled in the art will also recognize that multifunctional alcohols, thiols and amines may be used as co-initiator and even polyols and other macromolecules with suitable end group functionalities.

Another embodiment of the invented method is characterized in that the amount of metal originating from the catalyst ranges between 1 ppm and 2000 ppm. This amount of metal may be assessed via elemental analysis techniques known in the state of the art. If this amount is chosen above 2000 ppm, the method suffers from the disadvantage that the reaction control is insufficient and that the risk of runaway polymerization becomes unacceptably high. Furthermore, discoloration and racemization will become more pronounced. If the amount of catalyst is chosen below 1 ppm, the reaction times for manufacturing PLA become too long. A good compromise between both disadvantages is found in case that the amount of catalyst in the reaction mixture is chosen between 10 ppm and 1000 ppm.

A further embodiment of the method according to the invention is characterized in that the temperature of the liquid phase ranges between 160° C. and 220° C. In case that the temperature is chosen below 160° C., the execution of a continuous melt-polymerization of pure homopolymers like PDLA (containing exclusively D-lactoyl moieties) and PLLA (containing exclusively L-moieties) becomes very difficult due to crystallization phenomena in the reaction mixture. If temperature is chosen above 220° C., the risk of undesired degradation reactions and discoloration phenomena become reality. A good compromise for both disadvantages is achieved in case that the temperature in the reaction mixture ranges between 170° C. and 210° C.

Still another embodiment of the invented method is characterized in that the liquid phase is subjected to a devolatilization step before solidifying the formed polylactide. Remaining unbound lactide contained in the polymer in liquid phase may be removed by means of such a devolatilization step. The devolatilization step may be performed by means of a lowering of the pressure in the polymer in liquid phase, preferably below 10 mbar. Additionally, it is possible to purge inert gas through the polymer in liquid phase. Preferably an end-capping agent may be added to the polymer in liquid phase before applying the devolatilization step and the addition of the deactivation agent after the devolatilization step. Such end-capping agent prevents the depolymerization of the polymer especially from the hydroxyl-end group of the polyester by a back-biting mechanism.

Also interesting is the embodiment of the method according to the invention which is characterized in that a catalyst deactivating agent is added to the liquid phase when at least 90% of the lactide is converted into polylactide. This measure prevents depolymerization of the reaction product. Such depolymerization by the same catalyst may occur when the equilibrium conditions between free lactide (and possible other reactants) and the polymerization product are changed. This is the case when the temperature of the reaction mixture is lowered, or when the pressure is lowered at constant temperature. The deactivation is performed by the addition of a catalyst deactivating agent. In the known method using Sn-octoate as catalyst, peroxides are used for this purpose. Other suitable deactivating agents known from literature are phosphorus- and phosphite-containing compounds.

The invention also relates to the use of a specific metal coordination compound as a polymerization catalyst to convert lactide in liquid phase to polylactide. This metal coordination compound is represented by the structure II:

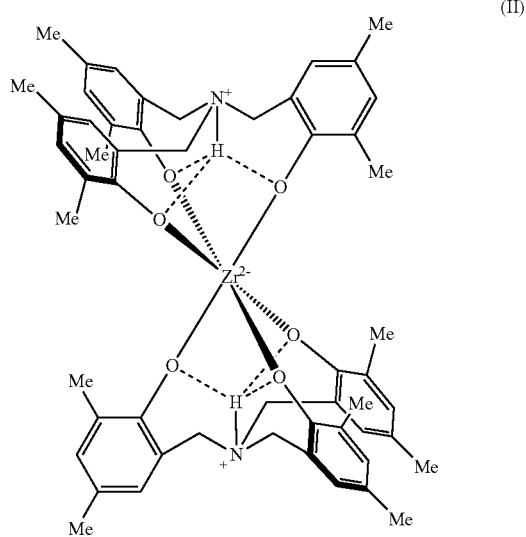

(II)

The invention also relates to polylactide containing a Zr-containing compound, with the amount of Zr metal originating from the compound ranging between 1 and 2000 ppm. This polylactide shows the desired properties obtained by its manufacture according to the present invention. The amount of Zr in the polylactide matrix is determined by means of elemental analysis techniques known from the state of the art.

The invention further relates to polylactide containing an amount of Zr-containing compound with the amount of Zr metal originating from that compound is approximately 1-2000 ppm and whereby the racemization rate of the lactoyl units within the polylactide during its manufacture is less than 2%. This feature of a low racemization rate shows that the polylactide according to the present invention is especially useful for applications at relative high temperatures.

BRIEF DESCRIPTION OF THE INVENTION

These and other aspects of the invention will be apparent from and elucidated with reference to the embodiments described hereinafter.

Figure 2:
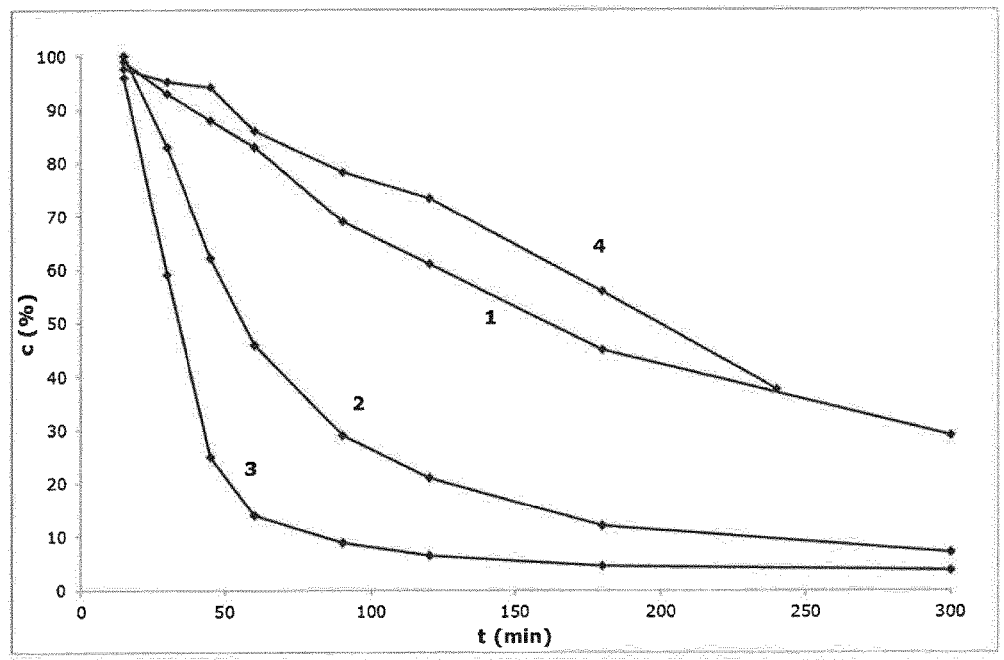
Figure 3:
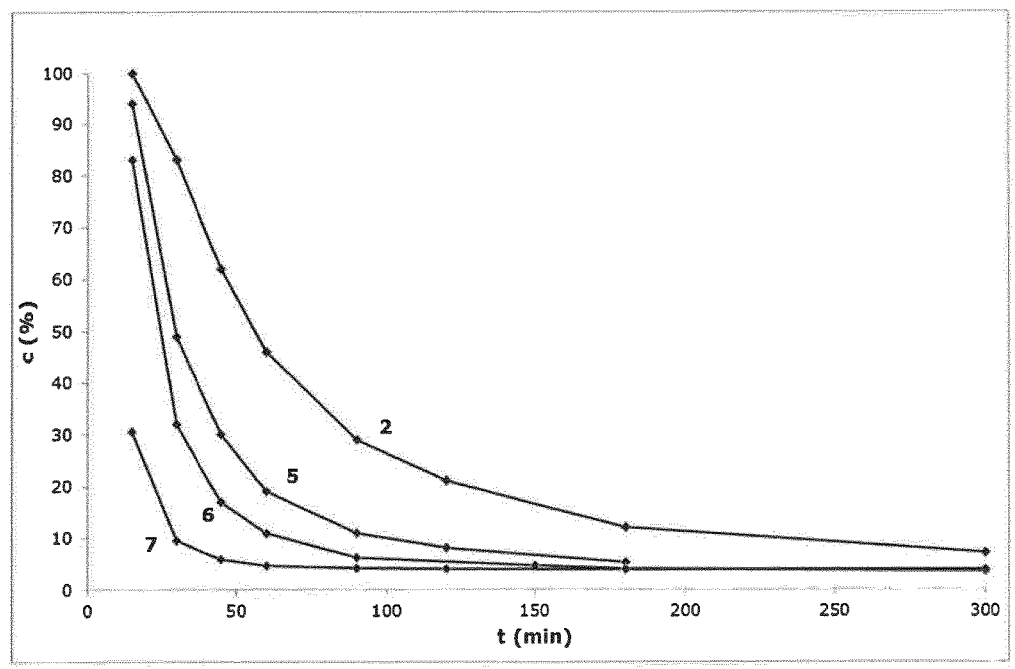
Figure 4:
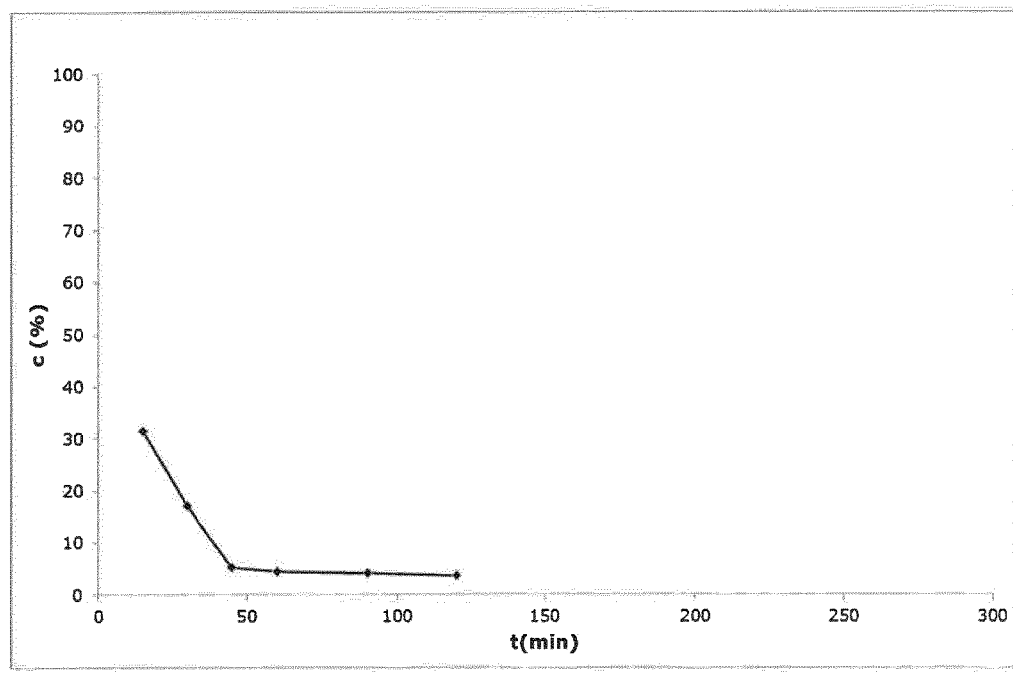

In the drawings:

FIG. 1 shows the reaction sequence used in the preparation of the ligand tris(-3,5-dimethyl-2-hydroxybenzyl) amine, FIG. 2 shows several conversion curves indicating the reaction kinetics of the polylactide manufacture using the new catalyst system according to the present invention, FIG. 3 shows several additional conversion curves indicating the reaction kinetics of the polylactide manufacture using the new catalyst system according to the present invention, and FIG. 4 shows a conversion curve indicating the reaction kinetics of the polylactide manufacture using a catalyst system not according to the present invention.

DETAILED EMBODIMENTS OF THE INVENTION

Methods of Analysis.

Absolute molecular weights were determined using gel permeation chromatography (GPC) measurements in hexafluoroisopropanol (HFIP) using a triple detection system (Viscotek GPC Max VE2001), equipped with a light scattering detector, viscosity detector and refractive index detector. Relative molecular weights reported were measured using chloroform as the eluent, a light scattering detector (LALLS) and against narrowly disperse polystyrene standards.

The stereochemical purity of the polymers was determined by a destructive method of derivatization to R- and S-methyllactates using an ion-exchange resin. The ratio of R- and S-lactates is subsequently detected using Gas Chromatography.

Residual lactide levels are detected by a HPLC method after precipitation of the PLA fraction. To the person skilled in the art it is however evident that many other techniques can be used to determine the amount of lactide in PLA, for example FTIR, n-IR and $^1$H-NMR.

Catalyst Manufacture

The ligands are manufactured according to the reaction sequence shown in FIG. 1. In this manufacture, hexamethylenetetramine (0.94 g, 6.66 mmol) is added to a mixture of 2,4 di-substituted phenol (80 mmol) and paraformaldehyde (3.00 g, 100 mmol). The solution is then refluxed for 48 hours and the resulting white powder recrystallized from methanol and ether.

The Hf- and Zr-coordination compounds for use in the invented method are manufactured essentially according to the Experimental section of the article "Isolation and characterisation of transition and main group metal complexes supported by hydrogen-bonded zwitterionic polyphenolic ligands" in Chem. Commun., 2003, 1832-1833. In general, one reacts the metal isopropoxide—for example, Zr(OiPr)$_4$·HOiPr—in equimolar amounts with the ligand at room temperature for two hours and the product is obtained after (re)crystallization. Adaptation of the amounts of compounds, for example for producing the hafnium compounds, is well within the daily routine of persons skilled in this field of technology. The Hf- and Zr-coordination compounds obtained after recrystallization from hot toluene were used in the polymerization experiments. It has been demonstrated that the recrystallized compounds have excellent air stability.

Polylactide Manufacture

Example 1

In a 1 L stainless steel batch reactor, 500 g L-lactide (PuraLact L®, Purac) was molten under nitrogen atmosphere and heated to 130° C.; a lactide melt sample of about 10 g was withdrawn for feed material analysis. Upon reaching 130° C., 0.15 g of Zr-catalyst complex II or 308 ppm was transferred into the reactor as a powder. The polymerizing melt was allowed to heat to 180° C. and the polymerization proceeded for 5 hours, while samples were taken after set time intervals to determine kinetics and the evolution of molecular weight. The absolute $M_w$ was determined to be 94 kg/mol at a conversion of 71%. $M_w$ versus PS was 256 kg/mol. The optical purity of the polymer was 99.4% L.

Example 2

A polymerization was performed according to the procedure mentioned in Example 1, but the amount of Zr-catalyst complex II employed was 0.33 g or 676 ppm. The absolute $M_w$ of the final PLA was determined to be 167 kg/mol at a conversion of 93%. $M_w$ versus PS was 358 kg/mol. The optical purity of the polymer was 99.2% L.

Example 3

Another polymerization was performed according to the procedure mentioned in Example 1, but the amount of Zr-catalyst complex II employed was 0.66 g or 1345 ppm. The absolute $M_w$ of the final PLA was determined to be 134 kg/mol at a conversion of 96%. $M_w$ versus PS was 276 kg/mol. The optical purity of the polymer was 99.0% L.

Example 4

In a 1 L stainless steel batch reactor, 500 g L-lactide (PuraLact L®, Purac) was molten under nitrogen atmosphere and heated to 130° C.; a lactide melt sample of about 10 g was withdrawn for feed material analysis. Upon reaching 130° C., 0.36 g 1-hexanol or 0.07 wt % was added as co-initiator. Next, 0.22 g Hf($^{tBu}$L) OiPr. HOiPr or 450 ppm was transferred into the reactor as a powder. The polymerizing melt was allowed to heat to 180° C. and the polymerization proceeded for 4 hours, while samples were taken after set time intervals to determine kinetics and the evolution of molecular weight. The $M_w$ of the final PLA was determined versus polystyrene standards to be 64 kg/mol at a conversion of 62%. The optical purity of the polymer was 99.2% L.

Example 5

In a 1 L stainless steel batch reactor, 500 g L-lactide (PuraLact L®, Purac) was molten under nitrogen atmosphere and heated to 130° C.; a lactide melt sample of about 10 g was withdrawn for feed material analysis. Upon reaching 130° C., 0.37 g 1-hexanol or 0.08 wt % was added as co-initiator. Next, 0.32 g of Zr-catalyst complex II or 640 ppm was transferred into the reactor as a powder. The polymerizing melt was allowed to heat to 180° C. and the polymerization proceeded for 5 hours, while samples were taken after set time intervals to determine kinetics and the evolution of molecular weight. The absolute $M_w$ of the final PLA was determined to be 114 kg/mol at a conversion of 95%. $M_w$ versus PS was 234 kg/mol. The optical purity of the polymer was 99.5% L.

Example 6

A polymerization was performed according to the procedure mentioned in Example 4, but the amount of co-initiator 1-hexanol employed was 0.72 g or 0.15 wt %. The absolute $M_w$ of the final PLA was determined to be 88 kg/mol at a conversion of 96%. $M_w$ versus PS was 182 kg/mol. The optical purity of the polymer was 99.6% L.

Example 7

A polymerization was performed according to the procedure mentioned in Example 4, but the amount of co-initiator 1-hexanol employed was 3.54 g or 0.73 wt %. The absolute $M_w$ of the final PLA was determined to be 24 kg/mol at a conversion of 96%. $M_w$ versus PS was 47 kg/mol. The optical purity of the polymer was 99.8% L.

Comparative Example 1

In a 1 L stainless steel batch reactor, 500 g L-lactide (PuraLact L®, Purac) was molten under nitrogen atmosphere and heated to 130° C.; a lactide melt sample of about 10 g was withdrawn for feed material analysis. Upon reaching 130° C., 0.4 g 1-hexanol or 0.08 wt % was added as co-initiator. Next, 0.15 g tin octoate ($Sn(C_8H_{15}O_2)_2$) or 300 ppm was transferred into the reactor as a powder. The polymerizing melt was allowed to heat to 180° C. and the polymerization proceeded for three hours, while samples were taken after set time intervals to determine kinetics and the evolution of molecular weight. The $M_w$ of the final PLA versus polystyrene was determined to be 242 kg/mol at a conversion of 96%.

FIG. 2 shows a number of typical curves indicative of the reaction kinetics of the polylactide manufacture using the new catalyst system of Examples 1-4 according to the present invention. More particularly, this Figure shows the concentration c (in weight percentage) of lactide in the polymerization mixture as a function on time (t) at a reaction temperature of 180° C., all based on a series of analyses as described above. From these data it can be concluded that the dosing level of the catalyst determines the polymerization rate: the higher the loading level, the faster polymerization occurs. It is clear that within the chosen range of hundreds of ppm catalyst, high conversions in a matter of hours can be achieved.

FIG. 3 shows an additional number of typical curves indicative of the reaction kinetics of the polylactide manufacture using the new catalyst system of Examples 2, 5, and 7 according to the present invention. More particularly, this Figure shows the concentration c (in weight percentage) of lactide in the polymerizing mixture as a function on time t (in minutes) at a reaction temperature of 180° C., all based on a series of analyses as described above. From these data it can be concluded that the use of a co-initiator further increases the polymerization rate. The higher the co-initiator loading, the higher polymerization rates are observed).

From Table 1, it can also be concluded that the co-initiator may be used to control the molecular weight of the polylactide. Molecular weights can be reached that provide access to most polymer applications.

TABLE 1

| Example | Amount of co-initiator (wt %) | $M_w$ (relative to PS, kg/mol) |
| --- | --- | --- |
| 2 | 0 | 358 |
| 5 | 0.08 | 234 |
| 6 | 0.15 | 182 |
| 7 | 0.73 | 47 |

FIG. 4 shows a typical polymerization conversion curve for a 300 ppm tin octoate catalyzed polymerization, according to the Comparative Example 1. From combined FIGS. 3 and 4 it is concluded that the new Zr-catalysts described in

The invention claimed is:

1. A method for manufacturing polylactide, comprising the steps of mixing lactide and a metal-coordination compound as polymerization catalyst to obtain a reaction mixture, polymerizing the lactide at a temperature of at least 150° C. to form polylactide in liquid phase and allowing the polylactide to solidify, characterized in that the polymerization catalyst comprises a metal-ligand coordination compound whereby the parent ligand answers the formula (I),

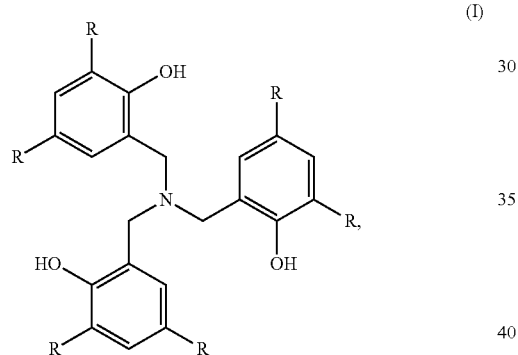

whereby R represents an H atom, an aliphatic group, a halide atom or a nitro group, the metal is at least one of Zr and Hf, and the amount of metal originating from the catalyst ranges between 1 and 2000 ppm of the reaction mixture and the racemization rate of the lactoyl units within the polylactide during the method of manufacture is less than 2%.

2. The method according to claim 1, characterized in that the R group is a methyl group.

3. The method according to claim 1, characterized in that the metal is Zr.

4. The method according to claim 1, characterized in that a co-initiator is added to the reaction mixture.

5. The method according to claim 1, characterized in that the temperature of the liquid phase ranges between 160° C. and 220° C.

6. The method according to claim 1, characterized in that the liquid phase is subjected to a devolatilization step before solidifying the formed polylactide.

7. The method according to claim 1, characterized in that a catalyst deactivating agent is added to the liquid phase when at least 90% of the lactide is converted into polylactide.

8. A method for manufacturing polylactide, comprising the steps of mixing lactide and a metal-coordination compound as polymerization catalyst to obtain a reaction mixture, polymerizing the lactide at a temperature of at least 150° C. to form polylactide in liquid phase and allowing the polylactide to solidify, characterized in that the polymerization catalyst comprises a metal-ligand coordination compound whereby the parent ligand answers the formula (I),

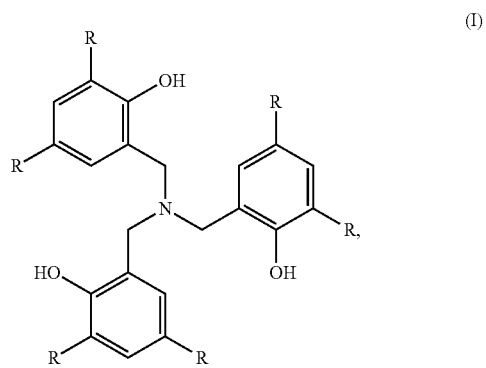

whereby R represents an H atom, an aliphatic group, a halide atom or a nitro group, the metal is at least one of Zr and Hf and, wherein the metal coordination compound is represented by structure (II)

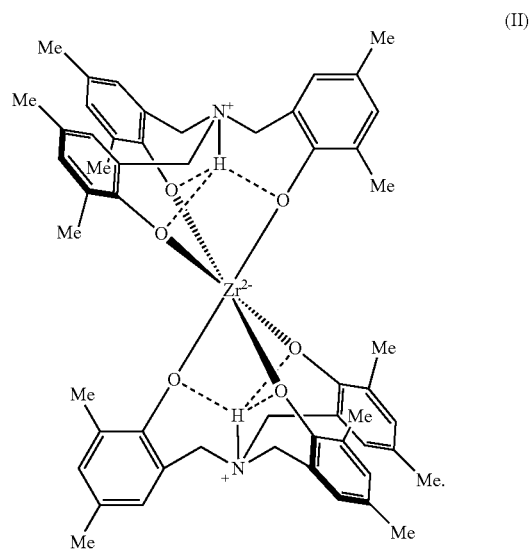

9. Polylactide containing a Zr-containing compound, characterized in that the amount of Zr metal originating from the compound is 1-2000 ppm and the racemization rate of the lactoyl units within the polylactide during its manufacture is less than 2%.

10. The method according to claim 2, characterized in that the metal is Zr.

11. The method according to claim 2, characterized in that a co-initiator is added to the reaction mixture.

12. The method according to claim 3, characterized in that a co-initiator is added to the reaction mixture.

13. The method according to claim 2, characterized in that the temperature of the liquid phase ranges between 160° C. and 220° C.

14. The method according to claim 3, characterized in that the temperature of the liquid phase ranges between 160° C. and 220° C.

15. The method according to claim 2, characterized in that the liquid phase is subjected to a devolatilization step before solidifying the formed polylactide.

16. The method according to claim 3, characterized in that the liquid phase is subjected to a devolatilization step before solidifying the formed polylactide.

17. The method according to claim 2, characterized in that a catalyst deactivating agent is added to the liquid phase when at least 90% of the lactide is converted into polylactide.

18. The polylactide according to claim 9, wherein the amount of Zr metal originating from the Zr-containing compound is 1-1000 ppm.

19. The method according to claim 1, wherein the metal is at least one of Zr and Hf, and the amount of metal originating from the catalyst ranges between 10 and 1000 ppm of the reaction mixture.

* * * * *